United States Patent
Boone et al.

(10) Patent No.: US 9,251,129 B2
(45) Date of Patent: Feb. 2, 2016

(54) METHOD, SYSTEM, AND COMPUTER-READABLE MEDIUM FOR CREATING A NEW ELECTRONIC DOCUMENT FROM AN EXISTING ELECTRONIC DOCUMENT

(71) Applicant: Nuance Communications, Inc., Burlington, MA (US)

(72) Inventors: Keith W. Boone, Randolph, MA (US); Sunitha Chaparala, South Weymouth, MA (US); Cameron Fordyce, Providence, RI (US); Sean Gervais, Dorchester, MA (US); Roubik Manoukian, Belmont, MA (US); Harry J. Ogrinc, Medfield, MA (US); Robert G. Titemore, Lexington, MA (US); Jeffrey G. Hopkins, Lincoln, RI (US)

(73) Assignee: Nuance Communications, Inc., Burlington, MA (US)

( * ) Notice: Subject to any disclaimer, the term of this patent is extended or adjusted under 35 U.S.C. 154(b) by 8 days.

(21) Appl. No.: 13/724,777

(22) Filed: Dec. 21, 2012

(65) Prior Publication Data

US 2013/0191737 A1 Jul. 25, 2013

Related U.S. Application Data

(60) Continuation of application No. 11/545,414, filed on Oct. 10, 2006, now Pat. No. 8,370,734, which is a division of application No. 10/448,320, filed on May 30, 2003, now Pat. No. 8,290,958.

(51) Int. Cl.
*G06F 17/00* (2006.01)
*G06F 17/24* (2006.01)
(Continued)

(52) U.S. Cl.
CPC ............ *G06F 17/24* (2013.01); *G06F 17/2229* (2013.01); *G06F 17/2247* (2013.01); *G06F 17/30595* (2013.01); *G06F 19/322* (2013.01); *G06Q 50/24* (2013.01); *G06F 19/3487* (2013.01)

(58) Field of Classification Search
CPC .................................. G06F 17/30; G06F 17/00
See application file for complete search history.

(56) References Cited

U.S. PATENT DOCUMENTS 4,477,698 A   10/1984   Szlam et al.
4,965,763 A   10/1990   Zamora
(Continued)

FOREIGN PATENT DOCUMENTS

| EP | 0584454 | | 3/1994 | |
| GB | 2372850 A | * | 9/2002 | ........ G06F 17/30206 |
| WO | WO 9530201 | | 11/1995 | |

OTHER PUBLICATIONS

U.S. Appl. No. 10/413,405, filed Apr. 15, 2003, Carus.
(Continued)

*Primary Examiner* — Farhan Syed
(74) *Attorney, Agent, or Firm* — Wolf, Greenfield & Sacks, P.C.

(57) ABSTRACT

A system and method may be disclosed for facilitating the creation or modification of a document by providing a mechanism for locating relevant data from external sources and organizing and incorporating some or all of said data into the document. In the method for reusing data, there may be a set of documents that may be queried, where each document may be divided into a plurality of sections. A plurality of section text groups may be formed based on the set of documents, where each section text group may be associated with a respective section from the plurality of sections and each section group includes a plurality of items. Each item may be associated with a respective section from each document of the set of documents. A selected item within a selected section text group may be focused. The selected item may be extracted to a current document. The current document may be exported to a host application.

17 Claims, 15 Drawing Sheets

(51) Int. Cl.
*G06F 17/22* (2006.01)
*G06F 17/30* (2006.01)
*G06F 19/00* (2011.01)
*G06Q 50/24* (2012.01)

(56) References Cited

U.S. PATENT DOCUMENTS

| | | | |
|---|---|---|---|
| 5,079,700 A | 1/1992 | Kozoll et al. | |
| 5,253,164 A | 10/1993 | Holloway et al. | |
| 5,325,293 A | 6/1994 | Dorne | |
| 5,327,341 A | 7/1994 | Whalen et al. | |
| 5,392,209 A | 2/1995 | Eason et al. | |
| 5,544,360 A | 8/1996 | Lewak et al. | |
| 5,664,109 A | 9/1997 | Johnson et al. | |
| 5,675,788 A * | 10/1997 | Husick | G06F 17/30017 |
| 5,799,268 A | 8/1998 | Boguraev | |
| 5,809,476 A | 9/1998 | Ryan | |
| 5,832,450 A | 11/1998 | Myers et al. | |
| 5,873,080 A | 2/1999 | Coden et al. | |
| 5,893,109 A | 4/1999 | DeRose et al. | |
| 5,893,717 A * | 4/1999 | Kirsch | G09B 7/00 434/118 |
| 5,970,463 A | 10/1999 | Cave et al. | |
| 5,974,412 A | 10/1999 | Hazlehurst et al. | |
| 6,006,221 A | 12/1999 | Liddy et al. | |
| 6,014,663 A | 1/2000 | Rivette et al. | |
| 6,021,202 A | 2/2000 | Anderson et al. | |
| 6,052,693 A | 4/2000 | Smith et al. | |
| 6,055,494 A | 4/2000 | Friedman | |
| 6,088,437 A | 7/2000 | Amick | |
| 6,182,029 B1 | 1/2001 | Friedman | |
| 6,192,112 B1 | 2/2001 | Rapaport et al. | |
| 6,289,353 B1 | 9/2001 | Hazlehurst et al. | |
| 6,292,771 B1 | 9/2001 | Haug et al. | |
| 6,347,329 B1 | 2/2002 | Evans | |
| 6,360,215 B1 | 3/2002 | Judd et al. | |
| 6,405,165 B1 | 6/2002 | Blum et al. | |
| 6,434,547 B1 | 8/2002 | Mishelevich et al. | |
| 6,438,533 B1 | 8/2002 | Spackman et al. | |
| 6,553,385 B2 | 4/2003 | Johnson et al. | |
| 6,560,620 B1 * | 5/2003 | Ching | G06F 17/27 707/999.202 |
| 6,684,188 B1 | 1/2004 | Mitchell et al. | |
| 6,810,410 B1 * | 10/2004 | Durham | G06F 9/44505 709/203 |
| 6,854,086 B2 | 2/2005 | Umen et al. | |
| 6,915,254 B1 * | 7/2005 | Heinze | G06F 17/27 382/225 |
| 6,947,936 B1 * | 9/2005 | Suermondt | G06F 17/30707 |
| 6,978,275 B2 | 12/2005 | Castellanos et al. | |
| 7,003,724 B2 * | 2/2006 | Newman | H04L 12/58 709/206 |
| 7,124,144 B2 | 10/2006 | Christianson et al. | |
| 7,165,073 B2 * | 1/2007 | Vandersluis | G06F 17/30389 |
| 7,287,031 B1 * | 10/2007 | Karpf | G06F 19/325 |
| 7,315,811 B2 | 1/2008 | Cote et al. | |
| 7,379,946 B2 | 5/2008 | Carus et al. | |
| 7,379,950 B2 * | 5/2008 | Sato | G06F 17/24 |
| 7,542,909 B2 | 6/2009 | Cote | |
| 7,568,149 B2 * | 7/2009 | Edwards | G06F 17/30899 715/205 |
| 7,617,121 B1 * | 11/2009 | DeMayo | G06F 17/30899 705/14.26 |
| 7,653,634 B2 | 1/2010 | Mathur | |
| 7,689,899 B2 * | 3/2010 | Leymaster | G06F 17/243 705/17 |
| 7,725,449 B2 * | 5/2010 | Naam | G06F 17/30864 707/706 |
| 7,774,196 B2 | 8/2010 | Cote et al. | |
| 7,783,474 B2 | 8/2010 | Cote et al. | |
| 7,912,700 B2 * | 3/2011 | Bower | G06F 3/0237 704/1 |
| 8,001,212 B2 * | 8/2011 | Letz | G06F 17/30938 709/217 |
| 8,073,830 B2 * | 12/2011 | Fontes | G06F 17/30864 707/706 |
| 8,296,666 B2 * | 10/2012 | Wright | G06F 17/30017 715/764 |
| 8,364,668 B2 * | 1/2013 | Khaliq | G06F 17/30873 707/726 |
| 8,793,162 B2 * | 7/2014 | King | G06K 9/00442 348/222.1 |
| 2002/0007285 A1 | 1/2002 | Rappaport | |
| 2002/0073157 A1 * | 6/2002 | Newman | H04L 12/58 709/206 |
| 2002/0095313 A1 | 7/2002 | Haq | |
| 2002/0143824 A1 | 10/2002 | Lee et al. | |
| 2002/0152244 A1 * | 10/2002 | Dean | G06F 17/2247 715/255 |
| 2002/0169764 A1 | 11/2002 | Kincaid et al. | |
| 2003/0046264 A1 | 3/2003 | Kauffman | |
| 2003/0061201 A1 | 3/2003 | Grefenstette et al. | |
| 2003/0079186 A1 | 4/2003 | Gondo et al. | |
| 2003/0109936 A1 * | 6/2003 | Umen | G06F 17/24 700/1 |
| 2003/0115080 A1 | 6/2003 | Kasravi et al. | |
| 2003/0154080 A1 | 8/2003 | Godsey et al. | |
| 2003/0172343 A1 * | 9/2003 | Leymaster | G06F 17/243 715/234 |
| 2003/0208382 A1 | 11/2003 | Westfall | |
| 2003/0233345 A1 | 12/2003 | Perisic et al. | |
| 2004/0103075 A1 | 5/2004 | Kim et al. | |
| 2004/0139400 A1 * | 7/2004 | Allam | G06F 17/212 715/201 |
| 2004/0186746 A1 | 9/2004 | Angst et al. | |
| 2004/0205638 A1 | 10/2004 | Thomas et al. | |
| 2004/0220895 A1 | 11/2004 | Carus et al. | |
| 2004/0243545 A1 | 12/2004 | Boone et al. | |
| 2004/0243551 A1 | 12/2004 | Boone et al. | |
| 2004/0243552 A1 | 12/2004 | Titemore et al. | |
| 2004/0243614 A1 | 12/2004 | Boone et al. | |
| 2005/0108010 A1 | 5/2005 | Frankel et al. | |
| 2005/0114122 A1 | 5/2005 | Uhrbach et al. | |
| 2005/0120020 A1 | 6/2005 | Carus et al. | |
| 2005/0120300 A1 | 6/2005 | Schwager et al. | |
| 2005/0144184 A1 | 6/2005 | Carus et al. | |
| 2005/0192792 A1 | 9/2005 | Carus et al. | |
| 2006/0069670 A1 * | 3/2006 | Khaliq | G06F 17/30554 |
| 2006/0122968 A1 * | 6/2006 | Naam | G06F 17/30696 |
| 2007/0239662 A1 * | 10/2007 | Fontes | G06F 17/30864 |
| 2008/0195388 A1 * | 8/2008 | Bower | G06F 3/0237 704/243 |
| 2008/0270573 A1 * | 10/2008 | Letz | G06F 17/30938 709/218 |
| 2009/0019358 A1 * | 1/2009 | Blake | G06F 17/2247 715/234 |
| 2009/0292698 A1 * | 11/2009 | Remy | G06F 17/30616 |
| 2010/0017390 A1 * | 1/2010 | Yamasaki | G06F 17/30646 707/E17.008 |
| 2011/0043634 A1 * | 2/2011 | Stegmann | B60R 1/00 348/148 |
| 2011/0310003 A1 * | 12/2011 | de la Barre | H04N 13/0402 345/156 |
| 2011/0310092 A1 * | 12/2011 | de la Barre | H04N 13/0409 345/419 |
| 2012/0224743 A1 * | 9/2012 | Rodriguez | G06T 11/60 382/103 |
| 2013/0191737 A1 * | 7/2013 | Boone | G06F 17/2229 715/256 |

OTHER PUBLICATIONS

U.S. Appl. No. 10/447,290, filed May 29, 2003, Boone.
U.S. Appl. No. 10/448,317, filed May 30, 2002, Boone.
U.S. Appl. No. 10/448,320, filed May 30, 2003, Boone.
U.S. Appl. No. 10/448,325, filed May 30, 2003, Titemore.
U.S. Appl. No. 10/787,889, filed Feb. 27, 2004, Carus.
U.S. Appl. No. 10/840,428, filed May 7, 2004, Carus et al.
U.S. Appl. No. 10/948,625, filed Sep. 23, 2004, Schwager.
U.S. Appl. No. 10/951,281, filed Sep. 27, 2004, Cote et al.
U.S. Appl. No. 10/951,291, filed Sep. 27, 2004, Uhrbach.
U.S. Appl. No. 10/953,448, filed Sep. 30, 2004, Carus.
U.S. Appl. No. 10/953,471, filed Feb. 29, 2004, Cote et al.

(56) References Cited

OTHER PUBLICATIONS

U.S. Appl. No. 10/953,474, filed Sep. 29, 2004, Frankel.
U.S. Appl. No. 11/007,626, filed Dec. 4, 2004, Cote et al.
U.S. Appl. No. 11/068,493, filed Feb. 28, 2005, Carus et al.
U.S. Appl. No. 11/069,203, filed Feb. 28, 2005, Cote et al.
Braithwaite, Continuity of Care Record (CCR) HL7 Board of Directors, http://www.hl7.org/library/himss/2004Orlando/ContinuityofCareRecord.pdf, undated.
Daelemans et al., TiMBL: Tilburg Memory Based Learner, version 5.0, Reference Guide, ILK Research Group Technical Report Series No. 04-02 (ILK-0402), ILK Research Group, Tilburg University, Tilburg, Netherlands, 2004.
Day, Extracting Knowledge from Text Using Learning by Constraint Relaxation (LCR), CSI, Florida Institute of Technology, www.csi-inc.com/CSI/pdf.jday_icim02.pdf, undated.
Gale et al., Discrimination Decisions for 100,000-Dimensional Spaces, Current Issues in Computational Linguistics, pp. 429-450, Kluwer Academic publishers, 1994.
HEIB, Research Note, NLP Basics for Healthcare, Gartner Research, Aug. 16, 2002.
Lee et al., Cleansing Data for Mining and Warehousing, Lecture Notes in Computer Science vol. 1677 archive, Proc. of the $10^{th}$ International Conference on Database and Expert Systems Applications, pp. 751-760, Springer-Verlag, London 1999.
McGregor, et al. "The e-baby data warehouse: a case study" System Sciences, 2002, HICSS, Proceedings of the $35^{th}$ Hawaii International Conference on Systems Sciences, Jan. 7-10, 2001, Piscataway, NJ, US, IEEE, Los Alamitos, CA, USA, Jan. 7, 2001, pp. 2871-2877.
Shalizi et al., Pattern Discovery in Time Series, Part I: Theory, Algorithm, Analysis and Convergence, J. of Machine Learning Research, (2002), Submitted Oct. 28, 2002, published 2002.
Smith et al., "MICROARRAS: An Advanced Full-Text Retrieval and Analysis System," ACM 1987, p. 187-195.
Song, et al., A Cognitive Model for the Implementation of Medical Problem Lists, Proceedings of the First congress on Computational medicine, Public health and Biotechnology, Austin, Texas, 1994.
Song, et al., A Graphical Interface to a Semantic Medical Information System, Journal of Foundations of Computing and Decision Sciences, 22(2), 1997.
Song, et al., A Graphical Interface to a Semantic medical Information System, Karp—95, Proceedings of the Second International Symposium on Knowledge Acquisition, Representation and Processing, pp. 107-109, 1995.
Van Rijsbergen, Information Retrieval, 2" Ed., Ch. 5, l3unerworths, London, 1979.
Waegemann, EHR vs. CCR: What is the difference between the electronic health record and the continuity of care record?, Medical Records Institute, 2004.
Yang et al. Faster algorithm of string comparison, Pattern Analysis and Applications, v. 6, No. 1, Apr. 2003: pp. 122-133.
Epic Web Training Manual, EpicWeb pp. 1-33, downloaded May 2, 2002.
http://www.comp.lancs.ac.uk/computing/research/stemming-general/index.htm downloaded Jul. 19, 2004.
http://www.comp.lancs.ac.uk/computing/research/stem-minglgeneral/stemmingerrors.htm downloaded Jul. 19, 2004.
http://www.comp.lancs.ac.uk/computing/research/stemming-general/performance.htm, downloaded Jul. 19, 2004.
Case Study: Massachusetts Medical Society, http://www.microsoft.com/resources/casestudies/CaseStudy.asp?CaseStudyID=14931, Jan. 13, 2004.
Press Release: Kryptiq Announces Support of CCR Initiative and Introduces New Solutions that Enable Information Portability, Accessibility and Clinical system Interoperability. http://www.kryptiq.com/News/PressReleases/27.html , downloaded Feb. 17, 2004.
Work Item Summary: WK4363 Standard Specification for the Continuity of Care Record (CCR), http://www.astm.org/cgi-bin/SoftCart.exe/DATABASE.CART/WORKTIEMS/WK4363.htm?E+mystore, Mar. 3, 2004.
Continuity of Care Record, American Academy of Family Physicians, http://www.aafp.org/x24962.xml?printxml posted Nov. 12, 2003.
Continuity of Care Record (CCR), AAFP Center for Health Infaimation Technology, http://www.centerforhit.org/x201.xml, posted Aug. 20, 2004.
Core Measures web page, Joint Commission on Accreditation of Healthcare Organizations, http://www.jcaho.org/pms/core+measures/, downloaded Mar. 22, 2004.
Code Information and Education web page, American Medical Association, http://www.ama-assn.org/ama/pub/category/3884.html, printed Mar. 22, 2004.
Category III CPT Codes, American Medical Association, http://www.ama-assn.org/ama/pub/article/3885-4897.html printed Mar. 22, 2004.
ICD-9-CM Preface (FY04), http://ftp.cdc.gov/pub/Health_Statistics/NCHS/Publications/ICD9-CM/2004/Prefac05.RTF.
ICD-9-CM Official Guidelines for Coding and Reporting, effective Oct. 1, 2003.
Hardware Reference Manual, Release 3 for DOS, revised Jan. 1994, PIKA Technologies, Inc., Ontario, Canada, available at http://www.piketechnologies.com/downloads/legac/AVA%20B-Series%20Hardware%20Manual.pdf, last accessed Jul. 25, 2005.
Customizing D/41 Call Analysis, date unknown, Intel Corp., Santa Clara, California, available at http://resource.intel.com/telecom/support/appnotes/custd41d.htm, last accessed Jul. 25, 2005.
Press Release: Kryptiq Announces Support of CCR Initiative and Introduces new Solutions that Enable Information Portability, Accessibility and Clinical System Interoperability, http://www.kryptig.corn/News/PressReleases/27.html, posted Feb. 17, 2004.
Work Item Summary: WK4363 Standard Specification for the Continuity of Care Record (CCR), http://www.astm.orWcgi-bin/SoftCart.exe/DATABASE.CART/WORKITEMS/WK4363.htm?E+mystore Mar. 3, 2004.
Hardware Reference Manual, Release 3 for DOS, revised Jan. 1994, PIKA Technologies, Inc., Ontario, Canada, available at http://www.pikatechnologies.com/downloads/legacy/AVA%20BSeries%20Hardware%20Manual.pdf (last accessed Jul. 25, 2005).
Customizing D/41 Call Analysis, date unknown, Intel Corp., Santa Clara, California, available at http://resource.intel.com/telecom/support/appnotes/custd41d.htm (last accessed Jul. 25, 2005).
Extended European Search Report from European Application 06786051 dated Jul. 8, 2010.
Examination Report and Supplementary European Search Report from European Application EP04753663, dated Dec. 20, 2007.

* cited by examiner

400

410

| Show Me | Any Discharge Sheet Admission Form | From | Last visit ▼ |

420 — Sections Viewer   ➕ ➖

⊟ Past History

| | Report Date | Type | Visit Date | Visit ID | Author |
|---|---|---|---|---|---|
| ⊞ | 03-06-2003 | Discharge | 03-06-2003 | samVIDB082403 | Alan |
| ⊟ | 03-03-2003 | Admission | 03-03-2003 | samVIDB082402 | Alan |

⊞ ☐ Past Surgical History
    ⊟ ☐ Past Medical History

☑ The patient is an 18 year old...
      ☑ He was closed reduced...
      ☑ He continues with median nerve...

⊞ ☐ Social History

⊟ Physical Examination

| | Report Date | Type | Visit Date | Visit ID | Author |
|---|---|---|---|---|---|
| ⊟ | 03-03-2003 | Admission | 03-03-2003 | samVIDB082402 | Alan |

⊞ ☐ Physical Examination on Admission
    ⊟ ☑ Physical Examination

☑ The patient is alert, oriented...

⊞ Assessment and Plan
⊟ Problems
  ☑ edema
  ☑ fracture
  ☑ neuropathy
⊞ Medications
⊟ Allergies
  ☐ Sulpha ▣ Done

| For | Yesterday ▼ | Dictated By | Me<br>Ema/Cardiology<br>Anyone/Radiology<br>Anyone | (Find) |

Reuse Draft  (Reuse) (Cancel) (Close)

☐ [Delete]  [move to ▼] [OK]
☐ Past History

☐ The patient is an 18-year-old, right-hand dominant male who had a motor vehicle accident on 10/03/02. He had a displaced right distal radius fracture and ulnar styloid fracture. He returns today for evaluation.
☐ He was closed reduced and maintained in a sugar-tong splint post injury and returns for evaluation.
☐ He continues with median nerve paresthesias in his thumb, index, principally his long finger, although he feels that this is slightly improved from his prior exam on 10/14/02.

☐ Physical Examination

☐ The patient is alert, oriented. Glasgow Coma Scale 15. Coherent, Temperature 96.9. Pulse 104. Blood pressure 170/124. Respiratory rate 12. Oxygen saturation of 100%.

☐ Assessment and Plan
☐ Problems

☐ The patient suffers from edema, fracture, and neuropathy.

☐ Medications
☐ Allergies

FROM FIG. 4A

My Computer

FIG. 4B

METHOD, SYSTEM, AND COMPUTER-READABLE MEDIUM FOR CREATING A NEW ELECTRONIC DOCUMENT FROM AN EXISTING ELECTRONIC DOCUMENT

CROSS-REFERENCE TO RELATED APPLICATIONS

This is a continuation application of U.S. Ser. No. 11/545,414, filed Oct. 10, 2006, which is a divisional application of U.S. Ser. No. 10/448, 320, filed May 30, 2003, which relates to U.S. patent application Ser. No. 10/413,405, filed Apr. 15, 2003, U.S. patent application Ser. No. 10/447,290, filed on May 29, 2003; U.S. patent application Ser. No. 10/448,317, filed on May 30, 2003; and U.S. patent application Ser. No. 10/448,325, filed on May 30, 2003. The disclosure of each such application is hereby incorporated by reference in its entirety where appropriate for teachings of additional or alternative details, features, and/or technical background, and priority is asserted from each.

BACKGROUND OF THE INVENTION

It may be generally known that various governmental agencies, businesses, health care institutions or other similar entities generate many reports. For example, a metropolitan police department may generate arrest reports for the people arrested by the members of the police department. In the medical industry, physicians, nurses and health care administrators generate voluminous patient records.

Often, the reports generated by these entities contain similar text. For example, a report generated by a police officer for a repeat offender may contain the same information with respect to address, history, etc. Another example may be reports generated by a primary care doctor and a referred specialist, which may contain the same information with regard to the reported health problem, health history, etc.

Conventional report generating systems may allow a user to reuse text contained in a previous report and apply that text to a current report. For example, a user may search a document library for the previous report and then 'cut-and-paste' the relevant sections from the previous report to the current report.

However, these conventional report generating systems have their drawbacks and disadvantages. For example, such typical report generating systems do not provide for a convenient method of focused searching of previous reports. Another drawback may be that the conventional systems do not organize information contained within multiple previous reports in a document library. Yet another drawback may be that conventional systems do not offer a mechanism to quickly add reusable material to a document.

SUMMARY OF THE INVENTION

An advantage exists in the present invention which facilitates the creation or modification of a document by providing a mechanism for locating relevant data from external sources and organizing and incorporating some or all of the data into the document.

Another advantage of the present invention includes facilitating the dictation of documents by providing a selection of data elements and/or text sections that have been automatically extracted from other documents that are likely to be relevant to the type of document being dictated. The present invention may allow a user to select which data elements and/or text sections are to be reused and where in the new document they should be inserted, automatically populating the new document with the data and text sections. An advantage exists in that valuable time may be saved when creating these new documents, and the present invention may be especially effective when substantial portions of the content of a new dictation is essentially a repeat of what has been stated before in previous dictations. An additional benefit of the present invention is that new dictations will likely be more complete, as importing data elements and text sections will prompt a user to highlight certain key information, which can lead to higher consistency and efficiency in future dictations. Another benefit may be access to data and/or text sections previously dictated by other third party users, which otherwise may not have been accessible.

As such, in a first aspect, the present invention includes an embodiment that relates to a method of reusing data. The method includes querying for a set of documents, where each document may be divided into a plurality of sections. The method also includes forming a plurality of section text groups based on the set of documents, where each section text group may be associated with a respective section from the plurality of sections and each section group includes a plurality of items. Each item may be associated with a respective section from each document of the set of documents. The method further includes focusing on a selected item within a selected section text group and extracting the selected item to a working draft document. The method yet further includes exporting the working draft document to a host application.

In a second aspect, the present invention includes an embodiment that pertains to a system for reusing data. The system includes at least one processor, a memory coupled to the at least one processor, a document library configured to be stored in the memory, and a reuse client configured to be stored as a computer programmable readable media in the memory and to be executed by the at least one processor. The document library comprises documents, where each document may be divided into a plurality of sections. The reuse client may be configured to query for documents in the document library and to form a plurality of section text groups based on the documents. Each section text group may be associated with a respective section from the plurality of sections and each section group comprises a plurality of items, where each item may be associated with a respective section from each document of the documents.

In a third aspect, the present invention includes an embodiment that relates to an apparatus for reusing data. The apparatus includes a means for querying for a set of documents, where each document may be divided into a plurality of sections. The apparatus also includes a means for forming a plurality of section text groups based on the set of documents, where each section text group may be associated with a respective section from the plurality of sections and each section group comprises a plurality of items. Each item may be associated with a respective section from each document of the set of documents.

In a fourth aspect, the present invention includes an embodiment that pertains to a computer readable storage medium on which may be embedded one or more computer programs. The one or more computer programs implements a method of reusing data. The one or more computer programs includes a set of instructions for querying for documents in a document library, where each document may be divided into a plurality of sections. The one or more computer programs also includes forming a plurality of section text groups based on the set of documents, where each section text group may be associated with a respective section from the plurality of sections and each section group comprises a plurality of items. Each item may be associated with a respective section from each document of the set of documents.

The above advantages and features are of representative embodiments only, and are presented only to assist in understanding the invention. It should be understood that they are not to be considered limitations on the invention as defined by the claims, or limitations on equivalents to the claims. Additional features and advantages of the invention will become apparent from the drawings, the following description, and the claims.

BRIEF DESCRIPTION OF THE DRAWINGS

While the specification concludes with claims particularly pointing out and distinctly claiming the present invention, it may be believed the same will be better understood from the following description taken in conjunction with the accompanying drawings, which illustrate, in a non-limiting fashion, the best mode presently contemplated for carrying out the present invention, and in which like reference numerals designate like parts throughout the figures, wherein:

FIGS. 4A-B illustrate a reuse viewer GUI provided by the reuse client module in accordance with yet another embodiment;

DETAILED DESCRIPTION OF THE EMBODIMENTS

For simplicity and illustrative purposes, the principles of the present invention are described by referring mainly to exemplary embodiments thereof. However, one of ordinary skill in the art would readily recognize that the same principles are equally applicable to, and can be implemented in, all types of network systems, and that any such variations do not depart from the true spirit and scope of the present invention. Moreover, in the following detailed description, references are made to the accompanying figures, which illustrate specific embodiments. Electrical, mechanical, logical and structural changes may be made to the embodiments without departing from the spirit and scope of the present invention. The following detailed description is, therefore, not to be taken in a limiting sense and the scope of the present invention is defined by the appended claims and their equivalents.

Embodiments of the present invention relate to data reuse. In particular, a reuse client module may be configured to provide to a user a reuse viewer graphical user interface (GUI) with a data filter component, a section viewer component, and a reuse draft component. The data filter component may be configured to provide the user the ability to search for a plurality of documents based on number of query parameters. In the set of retrieved documents, each document may be divided into sections and text may be associated with each section.

The reuse client module may be also configured to group together the text associated with the same section from each document in the set of documents. The reuse client module may be further configured to display the names of the plurality of the sections in a collapsed tree format in the section viewer component of the reuse viewer GUI. The reuse client module may also be further configured to display the associated text from each document when a section name may be expanded.

The reuse client may be further configured to display a draft document (or report) in the reuse draft component of the reuse viewer GUI, where the draft document displays the associated section names as displayed on the section viewer component. A user may hover over a section in the draft document and the selected section will highlight. The user may then select the corresponding section(s)/paragraph(s) in the section viewer component. The selected section(s)/paragraph(s) are then appended to the draft document. The reuse client module may be configured to send the draft document to a host application when the user may be finished.

Figure 1:
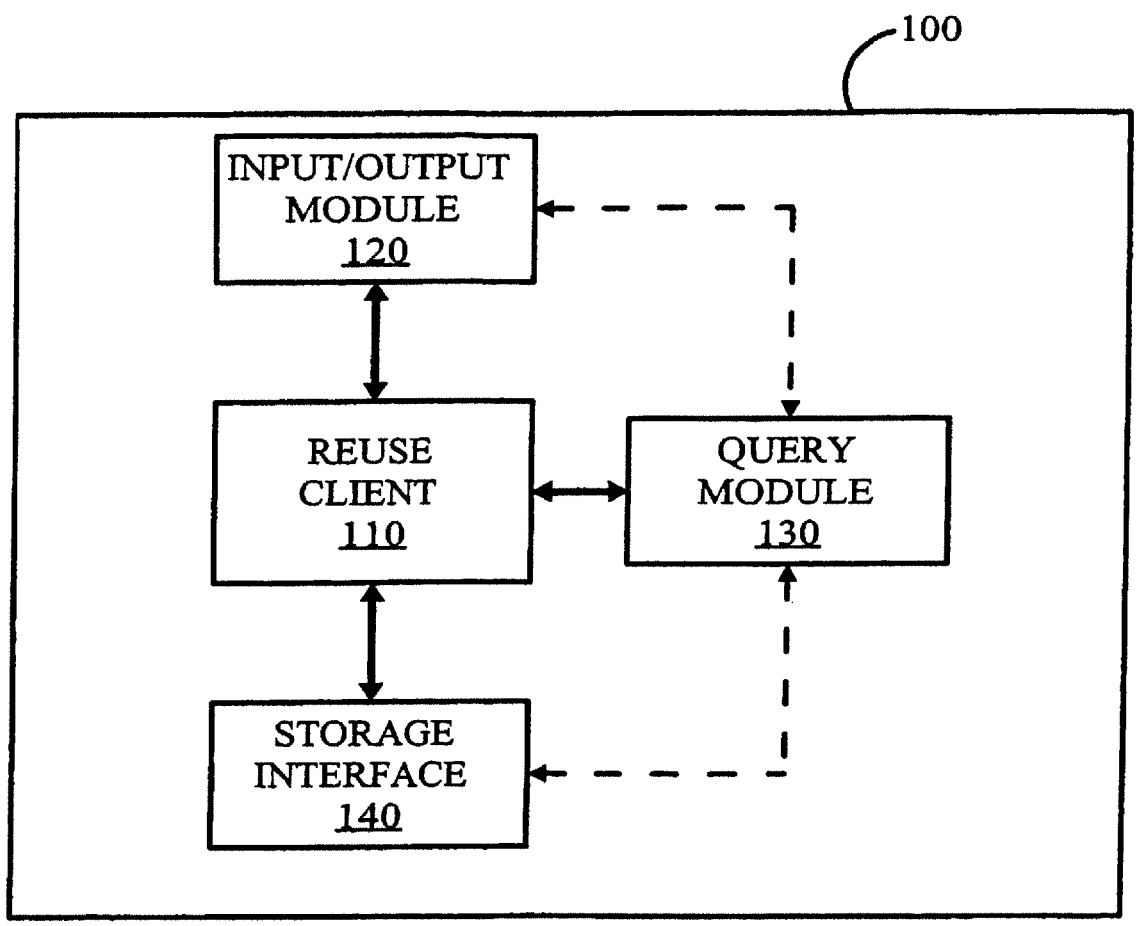
FIG. 1 illustrates an exemplary architecture of a reuse client module in accordance with an embodiment.

FIG. 1 illustrates an exemplary architecture of a reuse client module 100 in accordance with an embodiment. It should be readily apparent to those of ordinary skill in the art that the exemplary architecture depicted in FIG. 1 represents a generalized schematic illustration and that other components may be added or existing components may be removed or modified.

As shown in FIG. 1, the reuse client module 100 includes a reuse client 110, an input/output (I/O) module 120, a query module 130, and a storage interface 140. The reuse client 110 may be configured to provide the functionality for the reuse client module 100. For example, the reuse client 110 may be configured to perform actions in response to user input received through the I/O module 120. More specifically, the client reuse 110 may provide a user the capability to reuse data extracted from existing documents stored in a document library. The reuse client module 110 may present the extracted data in a manner that enables one to quickly incorporate the relevant extracted portions into a draft document.

The reuse client 110 may also be configured to interface with the 110 module 120. The 110 module 120 may be configured to provide a user interface for the user to utilize the reuse client module 110. More particularly, the reuse client 110 may invoke the I/O module 120 to provide an interface to query for document(s), to provide an interface to show extracted data from the found documents, and/or to provide an interface to show a draft document with extracted data selected for reuse. In other embodiments, the functionality of the I/O module 120 may be merged into the reuse client 110.

The reuse client 110 may be further configured to interface with the storage interface 140. The storage interface 140 may provide a mechanism for the reuse client module 100 to access existing documents for querying. The storage interface 140 may be a set of function calls, remote procedure calls or other similar interfaces.

The reuse client 110 may be further configured to interface with the query module 130. The query module 130 may receive query parameters from an interface generated by the I/O module 120 to search for a document or a set of documents. Alternatively, the query module 130 may receive the query parameters through the reuse client 110. The query module 130 may be configured to implement a search through either the storage interface 140 directly or through the reuse client 110 for the documents that match the received query parameters. For the matching documents, the query module may forward the matching documents to the reuse client 110. In other embodiments, the functionality of the query module 110 may be merged with the reuse client 110.

The reuse client module 100 may be implemented as a software program, a utility, a subroutine, or other similar programming entity. In this respect, the reuse client module 100 may be implemented using software languages such as C, C++, JAVA, etc. Alternatively, the reuse client module 100 may be implemented as an electronic device utilizing an application specific integrated circuit, discrete components, solid-state components or a combination thereof.

Figure 2:
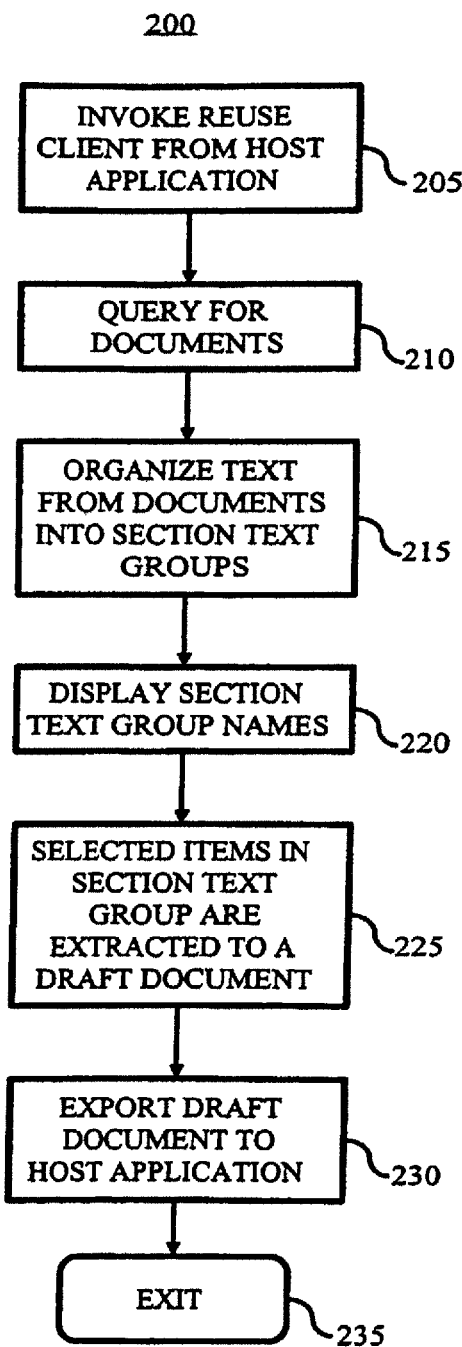
FIG. 2 illustrates an exemplary flow diagram for the reuse client in accordance with another embodiment.

FIG. 2 illustrates an exemplary flow diagram 200 for the reuse client 110 in accordance with another embodiment. It should be readily apparent to those of ordinary skill in the art that this method 200 represents a generalized illustration and that other steps may be added or existing steps may be removed or modified.

As shown in FIG. 2, a host application may invoke the reuse client module 100 by initiating a command, in step 205. Alternatively, the host application may have a menu item that represents the reuse client 100 or by a function call. Once invoked, the reuse client 110 may invoke the 110 module 120 to provide a graphical user interface for a user to input query parameters.

In step 210, the query module 130 may initiate a search for the requested documents based on the received query parameters. If matching documents are found, the query module 130 may forward the matching documents to the reuse client 110. Although not shown, if no matching documents are found, the query module 130 may notify the user of the lack of matching documents through the 110 module 120.

In step 215, the reuse client 110 may be configured to organize the retrieved document(s). More specifically, the documents are divided into a plurality of sections. The reuse client 110 may be configured to create a section group for each of the sections in the document. For each section, the reuse client may extract the text from the section from each of the documents and group the extracted text within the section group.

In step 220, the reuse client 110 may invoke the 110 module 120 to display the section groups in a collapsed tree format. The I/O module 120 may be configured to expand a section group in response to a user event. The I/O module 120 may then display the extracted text from the documents for the expanded section group.

In step 225, a user may select extracted text within an expanded section group. The reuse client 110 may then place the selected extracted text within a draft document provided by the I/O module 120.

In step 230, after completion of the selection extracted text, the reuse client 110 may export the draft document to the host application in response to another user event received through the 110 module 120. Subsequently, in step 235, the reuse client module 100 may exit.

Accordingly, a user may be presented with relevant document(s) for reuse through the reuse client module 110. Moreover, a user may quickly view relevant portions within the relevant document(s) to reuse in the user's current document.

Figure 3:
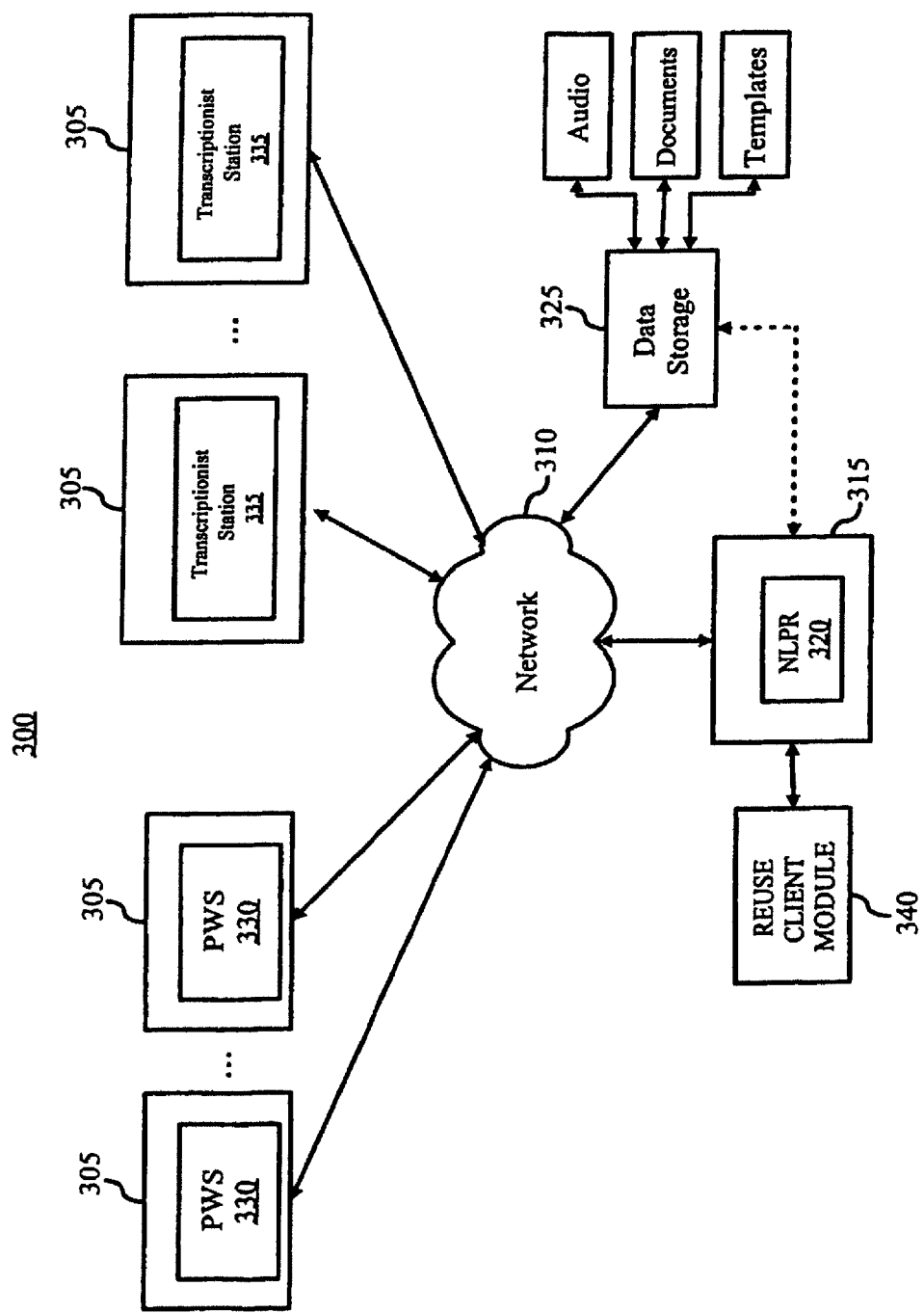
FIG. 3 illustrates a natural language patient record (NLPR) system utilizing a reuse client module in accordance with yet another embodiment.

FIG. 3 illustrates a natural language patient record (NLPR) system 300 utilizing a reuse client module in accordance with yet another embodiment. As shown in FIG. 3, the NLPR system 300 includes a plurality of workstations 305 interconnected by a network 310. The NLPR system 300 also includes a server 315 executing a computer readable version 320 of the NLPR system and data storage 325.

The workstations 305 may be personal computers, laptops, workstations, or other similar computing element. The workstations 305 execute a physician workstation (PWS) client 330 from the NLPR system 300. The PWS client 325 provide the capability for a physician to dictate, review, and/or edit medical records to the NLPR system 300.

The workstations 305 also execute a transcriptionist client 335 for a transcriptionist to access and convert audio files into electronic text. The NLPR system 300 may also use speech engines to automatically convert dictations from physicians into electronic text.

The network 310 may be configured to provide a communication channel between the workstations 305 and the server 315. The network 310 may be a wide area network, local area network or combination thereof. The network 310 may implement wired protocols (e.g., TCP/IP, X.25, IEEE802.3, IEEE802.5, etc.), wireless protocols (e.g., IEEE802.11, CDPD, etc.) or a combination thereof.

The server 315 may be a computing device capable of providing services to the workstations 305. The server 315 may be implemented using HP RX5670™, IBM xSeries205™, Sun Microsystem SunFire V1280™, or other similar computing platform. The server 315 may be configured to execute a computer readable version of the NLPR software 320. The NLPR software provides functionality for the NLPR system 300. The NLPR system 300 may receive audio files and/or documents by other network access means such as electronic mail, file transfer protocols, and other network transferring protocols.

The data storage 325 may be configured to interface with network 310 and provide storage services to the workstations 305 and the server 315. The data storage 325 may also be configured to store a variety of files such as audio, documents, and/or templates. In some embodiments, the data storage 325 includes a file manager (not shown) that provides services to manage and access the files stored therein. The data storage 325 may be implemented as a network-attached storage or through an interface through the server 315.

The server 315 may be further configured to interface with an embodiment of the reuse client module 340. A user may invoke the reuse client module 340 through a PWS client 320. For example, the reuse client module 340 may be a menu item on a graphical user interface of the PWS client 320. Alternatively, a user may use a command line prompt at the PWS client 320 to invoke the reuse client module. Once invoked, the reuse client module 340 may display a reuse viewer graphical user interface (GUI) as shown in FIGS. 4A-B.

FIGS. 4A-B illustrate a reuse viewer GUI 400 provided by the reuse client module 340 in accordance with yet another embodiment. It should be readily apparent that the elements of the reuse viewer GUI 400 may be deleted and/or modified and new elements added.

Figure 4C:
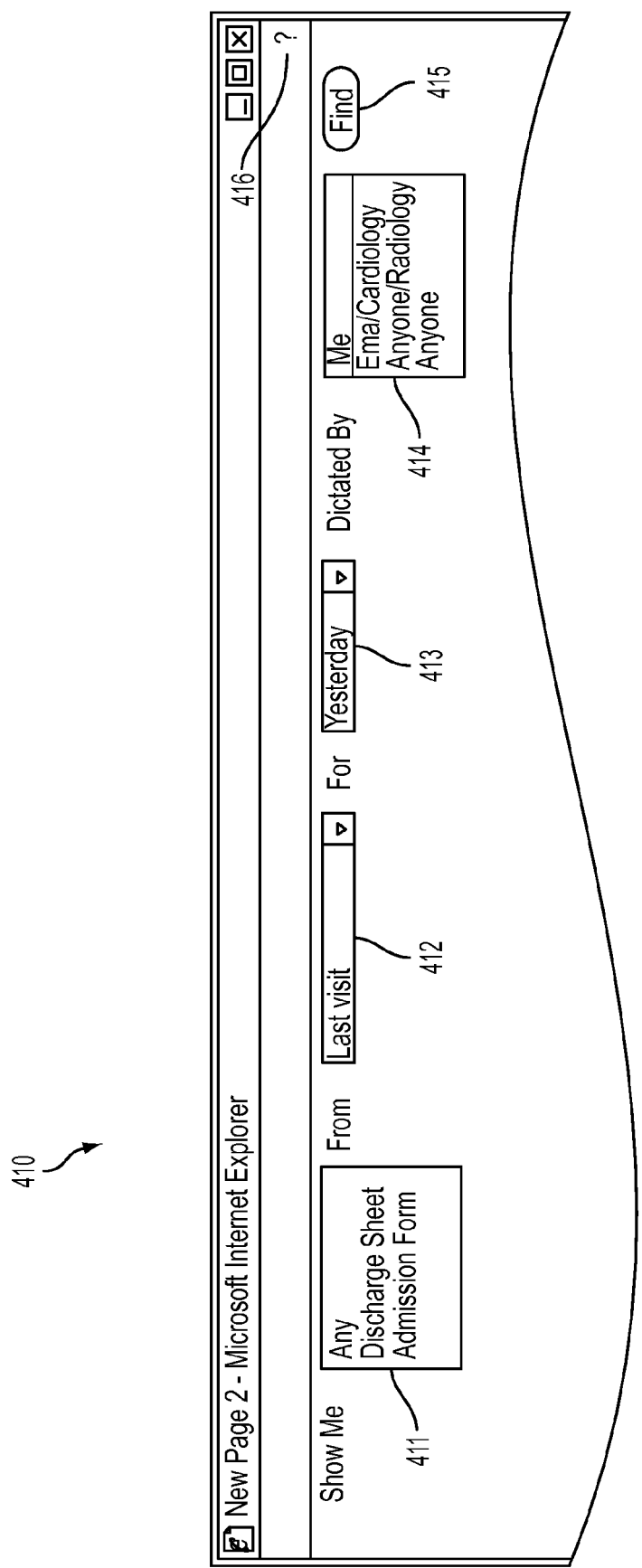
FIG. 4C illustrates a detailed view of the data filter component in accordance with yet another embodiment.

As shown in FIGS. 4A-B, the reuse viewer GUI 400 includes a data filter component 410, a section viewer component 420, and a reuse draft viewer 430. The data filter component 410 may be configured to display various query parameters to filter documents. For example, the data filter component 410 may display query options to filter medical records generated by the NLPR system 300 (shown in FIG. 3), which may be shown in greater detail in FIG. 4C.

FIG. 4C illustrates a detailed view of the data filter component 410 in accordance with yet another embodiment. As shown in FIG. 4C for this particular embodiment, the data filter component 410 includes filter (or query) parameters of 'Work-Type' parameter 411, 'Encounter' parameter 412, 'Time Frame' parameter 413, and a 'Dictated By' parameter 414. The work parameter 411 may be configured to have a variety of sub-parameters. For example, the Work Type parameter 411 may include an "Any" sub-parameter to find all records associated with a selected patient. The sub-parameters of Work Type parameter 411 may also include discharge sheet, admission form, or any other type of record generated for a patient.

The Encounter parameter 412 may be configured to locate the records associated with a type of visit for a patient. In that regard, the Encounter parameter 412 may have sub-parameters of "current visit", "last visit", "current and last visit", and/or "any visit" to assist in the scope of the search for records in the NLPR system 300.

The Time Frame parameter 412 may be configured to locate records within a specified block of time. Accordingly, the Time Frame parameter 412 may include sub-parameters of "yesterday", "last week", and/or "last 30 days" to assist in the scope of the search for records in the NLPR system 300.

The Dictated-By parameter 414 may be configured to locate records authored by a specific user. In that respect, the Dictated-By parameter 414 may include sub-parameters of "me", "anyone", "cardiology", "radiology" or any other department that has contact with a patient, to focus the scope of the search for records in the NLPR system 300.

The reuse viewer GUI 400 also includes a "Find" button 415 and a "Help" button 416. The Find button 415 may be configured to query or apply a data filter to the document database of the NLPR system 300. The results of the search are displayed on the section viewer component 420. The Help button 416 may be configured to display a window of instructions to assist the user in the operation of the reuse viewer GUI 400.

Figure 5:
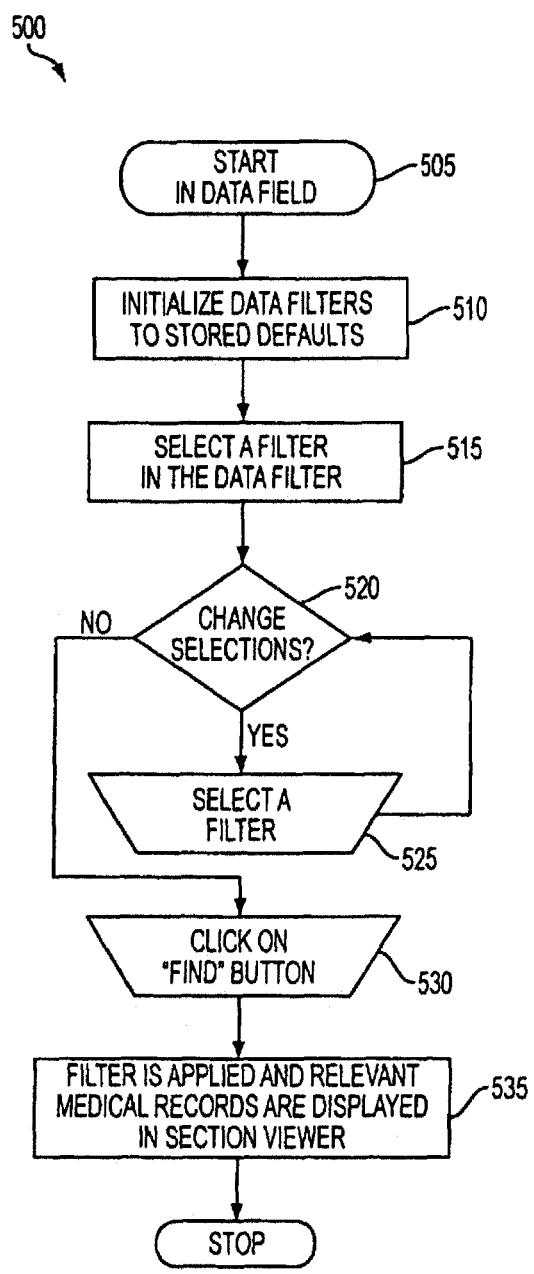
FIG. 5 illustrates a more detailed flow diagram for the data filtering component in accordance with yet another embodiment.

FIG. 5 illustrates a more detailed flow diagram 500 for the data filtering component 410 in accordance with yet another embodiment. It should be readily apparent to those of ordinary skill in the art that this flow diagram 500 represents a generalized illustration and that other steps may be added or existing steps may be removed or modified.

As shown in FIG. 5, the reuse client module 340 may be configured to initiate the data filter component 510, in step 505. More particularly, the reuse client module 340 may determine whether or not a user has specified personal (or customized) filter parameters. If a user has specified the use of customized filter parameters, the reuse client module 340 may be configured to retrieve the customized filter parameters from a predetermined location, e.g., a user profile, and display the customized filter parameters in the data filter component 510. Otherwise, the reuse client module 340 may be configured to display the default filter parameters in the data filter component 510.

In step 515, the reuse client module 340 receives an indication that the user has selected a filter parameter in the data filter component 410. For example, in the default display of the data filter component 410, the reuse client displays 'Work-type' filter, an 'Encounter' filter, a 'Time Frame' filter, and a 'Dictated Persons' filter. In step 520, the reuse client module 340 may determine if user has changed the value in the selected filter. If the user has changed the value, in step 525, the reuse client module 340 may store the parameter and return to step 520. More particularly, the reuse client module 340 may detect a change in the parameters of Work-type, Encounter, Time, and/or Dictated Persons filters. For example, a user may select "Last 30 Days" in the Time filter to query for documents. Otherwise, if the user has not changed the value, the reuse client module 340 may set the filter parameters to a default value, e.g., 'Any' value.

In step 530, the reuse client module 340 may be configured to receive an indication that the user has activated the 'Find' button. Subsequently, the reuse client module 340 may form a query (or filter) the document library with the set filter parameters as discussed above.

In step 535, the reuse client module 340 may be configured to retrieve the relevant documents from the document library and display the relevant documents in the section viewer component 420 of the reuse viewer GUI 400. If documents are not found, the reuse client module 340 may indicate to the user that the query failed to find relevant documents. Subsequently, the reuse client module 340 may be configured to exit the processing for method 500.

Returning to FIGS. 4A-13, the section view component 420 may be configured to display the results from a query initiated in the data filter component 410 in a tree-view like structure. The available sections for reuse and its contents are organized as paragraphs in a report-wise format. More particularly, the reuse client module 340 may be configured to organize the documents according to sections. Each document in the NLPR system 300 may be divided into sections. For each section, the reuse client module 340 may be configured to retrieve the associated text from that section in each of the retrieved documents. The retrieved associated text may be then organized as paragraphs under the section in the section viewer component 420, which may be illustrated in FIG. 6B.

Figure 6A:
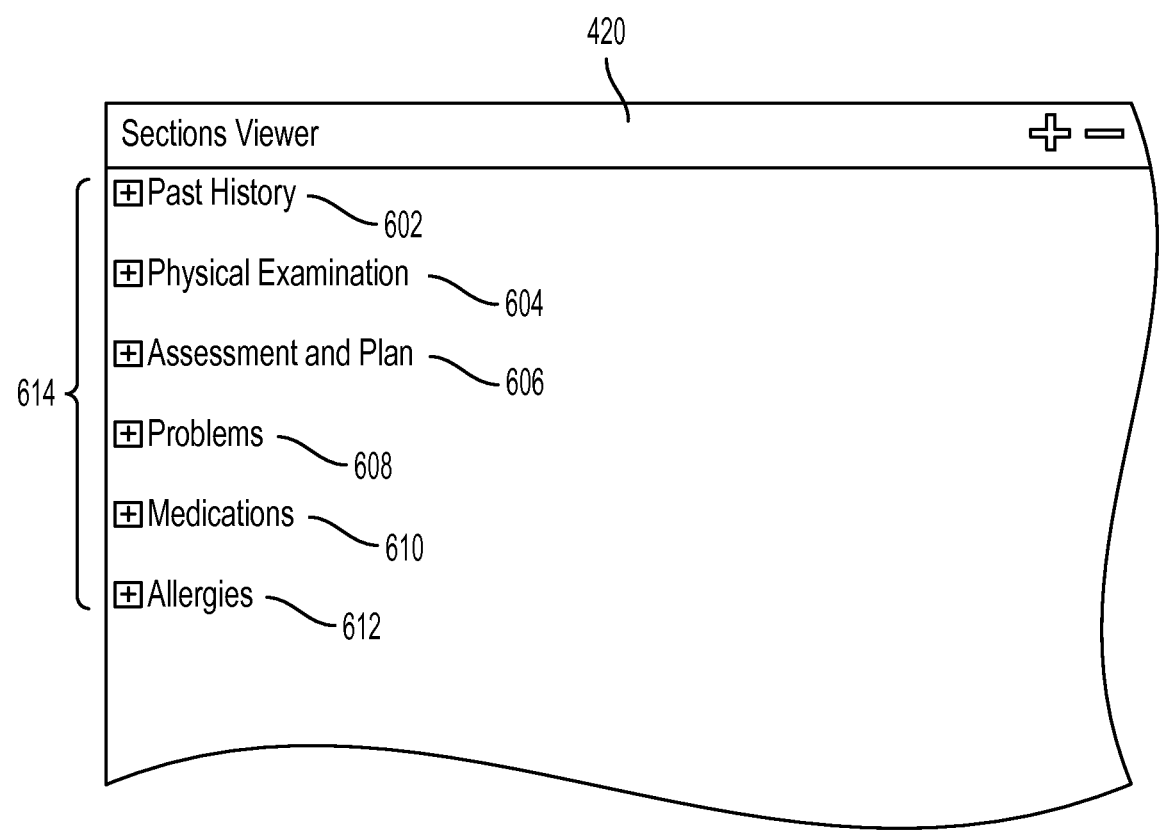
FIG. 6A illustrates a detailed view of the section view component in accordance with yet another embodiment.
Figure 6B:
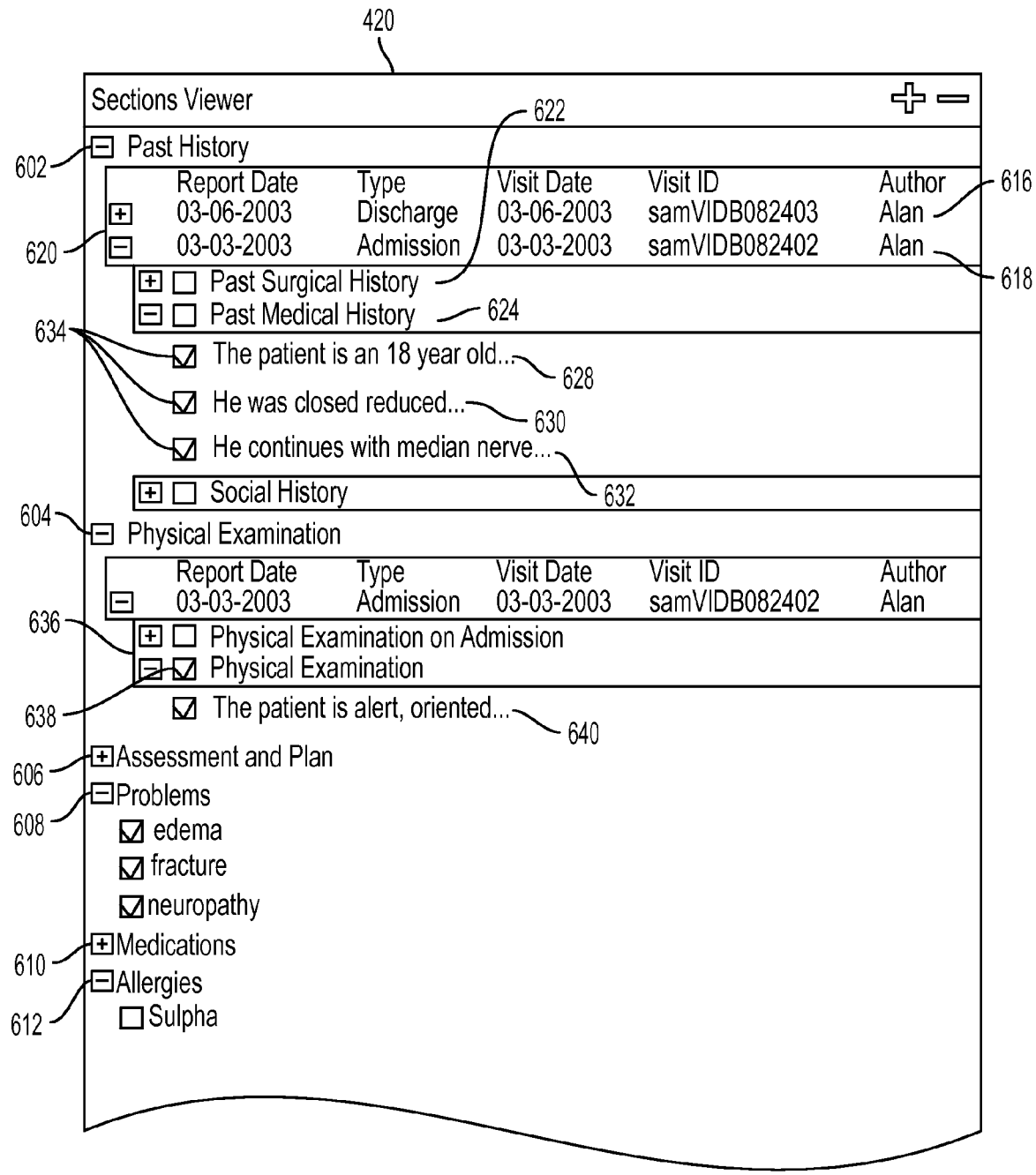
FIG. 6B illustrates a detailed view of the section view component in an expanded view in accordance with yet another embodiment.

FIG. 6A illustrates a detailed view of the section view component 420 in accordance with yet another embodiment. As shown in FIG. 6B, the section view component 420 initially displays sections names (Past History 602, Physical Examination 604, Assessment and Plan 606, Problems 608, Medications 610, and Allergies 612) as a top-level tree. Expand boxes 614 are also display with the associated section name.

When a section may be expanded, i.e., the selected expand box may be activated, the reuse client module 340 may be configured to display a list of reports pertaining to the selected section as the next level item of the tree, where the contents are organized as paragraphs, as illustrated with FIG. 6B.

FIG. 6B illustrates a detailed view of the section view component 420 in an expanded view in accordance with yet another embodiment. As shown in FIGS. 6A-B, the reuse client module 340 may be configured to display the relevant documents found by the data filtering component 410 organized by sections names. More particularly, the section view component 420 displays Past History 602 with two reports 616, 618. The two reports also include associated expand boxes 620.

In this particular view, a user has expanded the view on report 618 to show additional subsections 622, 624. The additional subsections also include associated expand boxes 626. The associated expand box for report 624 was activated to display the individual paragraphs 628, 630, 632. After activation of the expand boxes, the same expand boxes become collapse boxes to collapse the display.

The individual paragraphs 628-632 also include associated check boxes 634. The client reuse module 340 may be configured to append individual paragraphs 628-632 to a draft document in response to the check boxes being activated. The client reuse module may also append sections from a report. For example, Physical Examination 636 under Physical Examination 604 displays associated expand box 626 and associated check box 638. As shown, associated check box 638 may be checked, which then activates the check marks for check boxes 640 of the paragraphs in the subsection Physical Examination 636. The text from the Physical Examination 636 may then be appended to the draft document in response to the activation of check box 638.

Figure 7A:
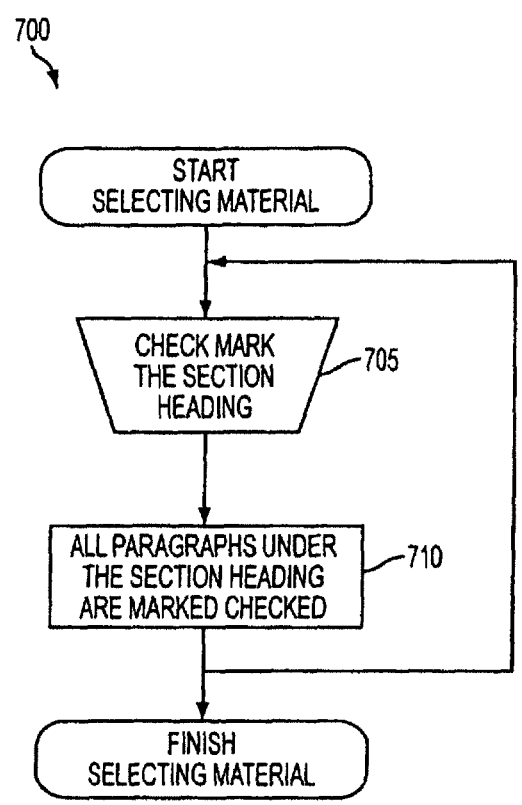
FIG. 7A illustrates a more detailed flow diagram for a section viewer component in accordance with another embodiment.

FIG. 7A illustrates a more detailed flow diagram 700 for section viewer component 420 in accordance with another embodiment. It should be readily apparent to those of ordinary skill in the art that this flow diagram 700 represents a generalized illustration and that other steps may be added or existing steps may be removed or modified.

As shown in FIG. 7A, the reuse client module 340 may receive an indication from the section viewer component 420 that the user has selected a section by activating the selected section, e.g., checking the check box, in step 705.

In step 710, the reuse client module 340 may be configured to select all the paragraphs under the selected section by checking the respective check boxes.

Figure 7B:
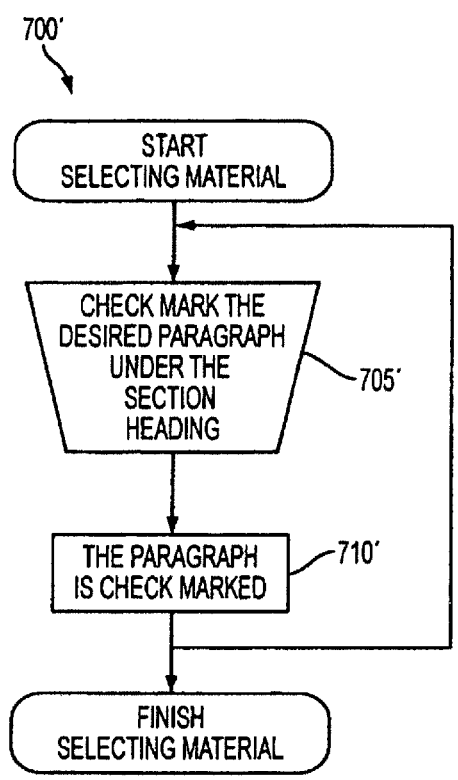
FIG. 7B illustrates a more detailed flow diagram for a section viewer component in accordance with another embodiment.

FIG. 7B illustrates a more detailed flow diagram 700' for section viewer component 420 in accordance with another embodiment. It should be readily apparent to those of ordinary skill in the art that this flow diagram 700' represents a generalized illustration and that other steps may be added or existing steps may be removed or modified.

As shown in FIG. 7B, the reuse client module 340 may be configured to receive indication that a user has selected a section by the expansion of the selected section in step 705'.

In step 710', the reuse client module 340 may be configured to receive indication that the user has selected a paragraph(s) with the selected section by the checking of the selected paragraph(s).

Returning to FIGS. 4A-B, the reuse draft component 430 may be configured to provide an at-a-glance view of all paragraphs and/or sections selected from the section view component 420 in a draft (or current) document. The reuse draft component 430 may also provide a user the capability to reuse paragraphs from one section in another section of a current report. An example of the reuse draft component 430 in conjunction with the section view component 420 may be illustrated in FIGS. 8A-B in accordance with yet another embodiment.

Figure 8A:
FIGS. 8A-B illustrate an exemplary display of the reuse draft component in conjunction with the section view component in accordance with yet another embodiment.
Figure 8B:
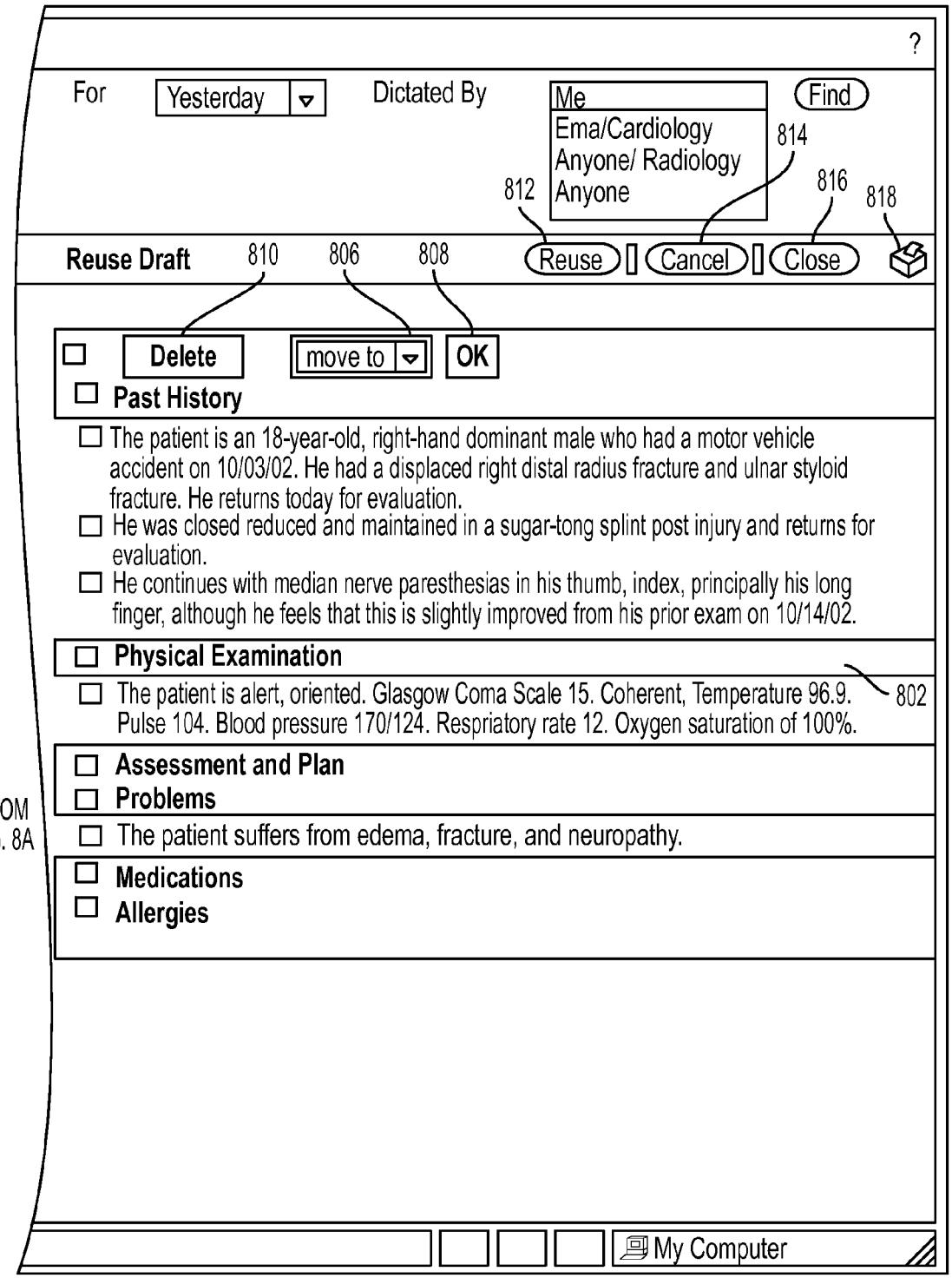

As shown in FIGS. 8A-B, the reuse client module 340 may be configured to highlight a Physical Examination section 802 when a user hovers over the Physical Examination section 802 with a cursor. The reuse client module 340 may display the paragraphs from the Physical Examination section 804 in the section viewer component 420. The reuse client module 340 may also be configured to append selected paragraphs to the current document displayed on the reuse draft component 430 in response to a selection of the selected paragraphs in the section viewer component 420.

The reuse draft component 430 also includes a 'Move-to' drop down box 806, an 'OK' button 808, a 'Delete' button 810, a 'Reuse' button 812, a 'Cancel' button 814, a 'Close' button 816, and a 'Print' icon 818. The Move-to drop down box 806 may be configured to move a highlighted paragraph to another section within the reuse draft component 430. More particularly, a user may activate the associated check box(es) for selected section(s). The user then selects a destination section in the Move-to drop down box 806. Subsequently, the user activates the OK button 808, which then removes the selected paragraphs from 808 and which may be configured to initiate the transfer from a source section to a destination section for the Move-to function.

The Delete button 810 may be configured to erase or remove highlighted paragraphs from the current document in the reuse draft component 430. More specifically, a user may activate the associated check box(es) for selected paragraph(s). The user then activates the Delete button 810 to delete the selected paragraph(s).

The Reuse button 812 may be configured to copy selected material to the host application. More particularly, the reuse client module 340 may copy the contents of the current document to the host application in response to the activation of the Reuse button 812. Subsequently, the reuse viewer GUI interface 400 closes and control returns the host application.

The Cancel button 814 may be configured not to implement any of the changes to a current document in the reuse draft component 430. More particularly, the reuse client 430 may clear the paragraph(s) copied to the reuse draft component 430 and return to the host application.

The Close button 450 may be configured to close the reuse viewer GUI 400. More specifically, the reuse client 340 may display a dialog window to advise a user that closing the reuse viewer GUI 400 will result in losing the current copied data. If the user selects to close the window, the reuse client module 340 initiates an exiting routine for the reuse viewer GUI 400. Otherwise, if the user decides not to cancel, the reuse client module 340 returns to the reuse viewer GUI 400.

Figure 9:
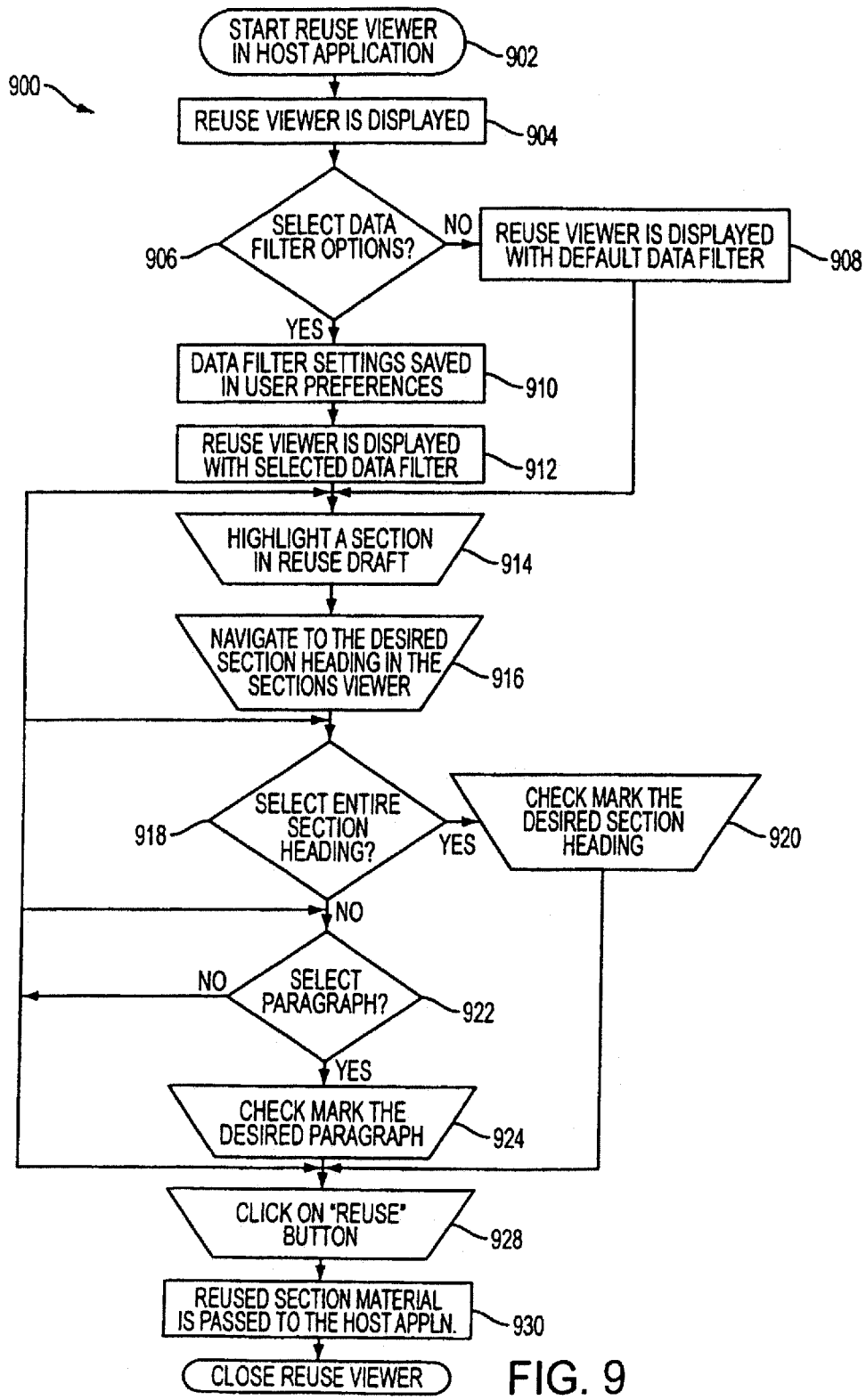
FIG. 9 illustrates a flow diagram of the reuse client module shown in FIG. 3 in accordance with yet another embodiment.

FIG. 9 illustrates a flow diagram 900 of the reuse client module 340 in accordance with yet another embodiment. It should be readily apparent to those of ordinary skill in the art that this flow diagram 900 represents a generalized illustration and that other steps may be added or existing steps may be removed or modified.

As shown in FIG. 9, the reuse client module 340 may be initiated by a host application, e.g., NLPR system 300, in step 902. More particularly, the host application may invoke the reuse client module by activating a menu item, an icon, command line prompt or other similar program initiation technique. The host application may specify attributes in the initiation of the reuse client module 340. For example, the NLPR system 300 specifies the attributes of provider, patient, dictated persons, and the sections to reuse. As another example, for a patent attorney system, the host application may specify the attributes of the client, dictated persons, and sections to reuse.

In step 904, the client reuse module 330 may display the graphical user interface such as the reuse viewer GUI 400.

In step 906, in displaying the data filter component 410, the reuse client module 340 may prompt a user of whether or not to select customized filter (or query) parameters that have been previously saved in a user preference profile, if the user decides not to use the customized filter parameters, the reuse client module 340 may display default filter parameters, e.g., parameters shown in FIG. 4C, in step 908. Otherwise, in step 910, the reuse client module 340 may retrieve the customized filter parameters from the user preference profile. In step 912, the reuse client module 340 may display the customized filter parameters on the data filter component 410. Subsequently, the reuse client module 340 may display the data filter component 410 with the appropriate data filter parameters, the section viewer component 420, and the reuse draft component 430.

In step 914, a user may highlight a section displayed on the reuse draft component 430. The reuse client module 340 may be configured to display the sections where reuse may be possible and in the order that the sections appear in the host application, in step 916.

In step 918, the reuse client module 340 may be configured to determine whether a user selected an entire section or selected paragraphs in response to a user activation of a section heading. If the user selected the entire section heading, the reuse client module 340 may mark the entire section as being used, in step 920. Otherwise, the reuse client module 340 determines whether or not an individual paragraph under the section heading has been selected, in step 922.

If the reuse client module 340 determines that a paragraph has not been selected, the reuse client returns to the processing of step 918. Otherwise, the reuse client module 340 may mark the selected paragraphs as check in the section view component 420, in step 922.

In step 924, the reuse client module may be configured to append the material with check marks to the current document displayed in the reuse draft component 430. Subsequently, the reuse client module 340 may prompt a user through a dialog box whether or not the user would like to modify the filter settings. If the reuse client module 340 receives indication that the user would like to modify the filter settings, the reuse client module 340 may filter for new documents in the document library of the NLPR system 300. The reuse client module 340 may display the newly filtered documents in the section viewer component 420 with appropriate markings for sections that have already been reused.

In step 928, when the reuse client module 340 receives indication that the Reuse button 446 has been activated, the reuse client module 340 may transfer the contents of the reuse draft section to the calling host application, e.g., the NLPR system 300. Subsequently, in step 930, the reuse client module 340 closes the reuse viewer GUI 400.

Figure 10:
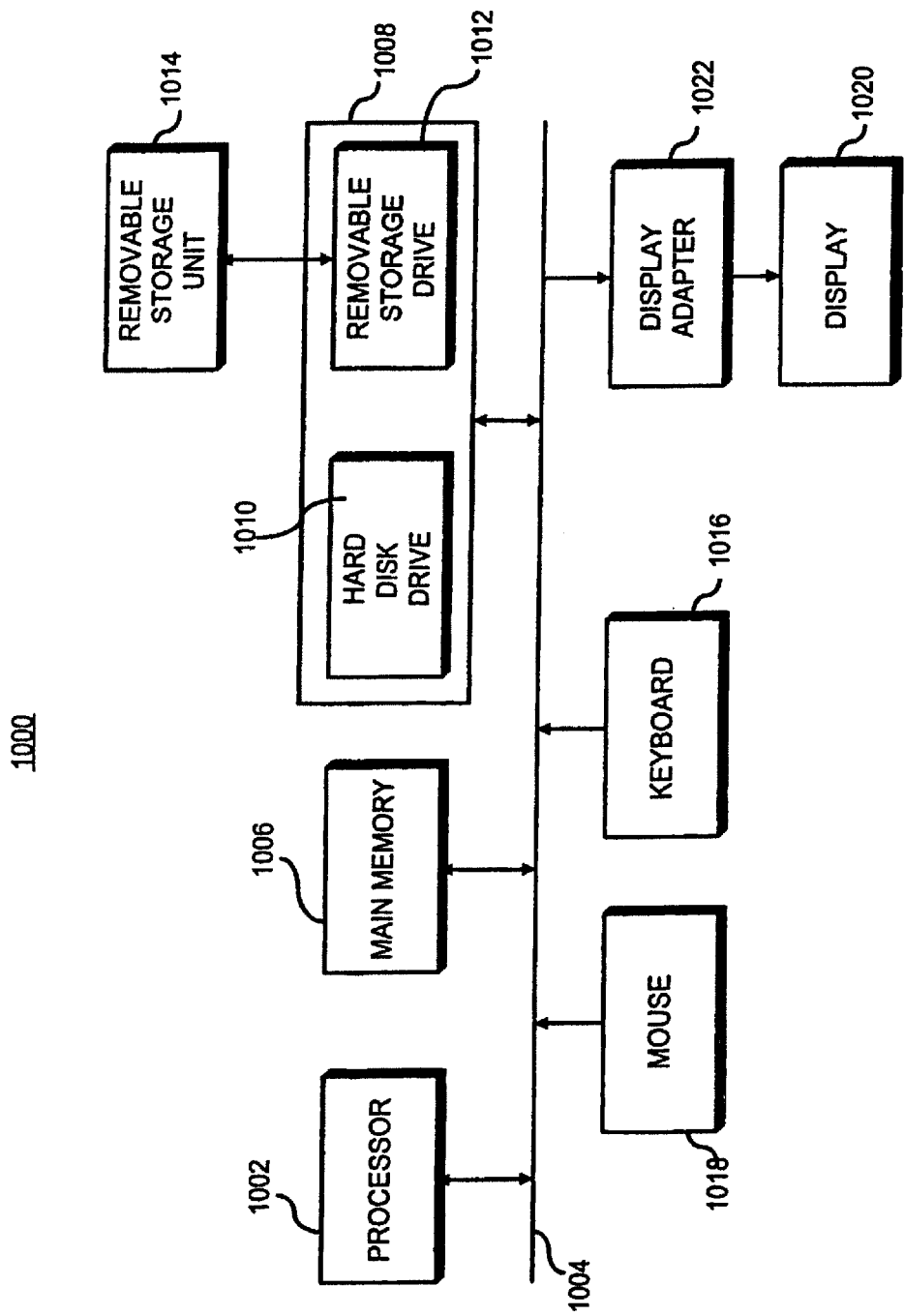
FIG. 10 illustrates an exemplary block diagram of a computer system where an embodiment may be practiced.

FIG. 10 illustrates an exemplary block diagram of a computer system 1000 where an embodiment may be practiced. The functions of the expressway routing module may be implemented in program code and executed by the computer system 1000. The reuse client module 340 and the NLPR system 300 may be implemented in computer languages such as PASCAL, C, C++, JAVA, etc.

As shown in FIG. 10, the computer system 1000 includes one or more processors, such as processor 1002, that provide an execution platform for embodiments of the expressway routing module. Commands and data from the processor 1002 are communicated over a communication bus 1004. The computer system 1000 also includes a main memory 1006, such as a Random Access Memory (RAM), where the software for the expressway routing module may be executed during runtime, and a secondary memory 1008. The secondary memory 1008 includes, for example, a hard disk drive 1010 and/or a removable storage drive 1012, representing a floppy diskette drive, a magnetic tape drive, a compact disk drive, etc., where a copy of a computer program embodiment for the expressway routing module may be stored. The removable storage drive 1012 reads from and/or writes to a removable storage unit 1014 in a well-known manner. A user interfaces with the expressway routing module with a keyboard 1016, a mouse 1018, and a display 1020. The display adaptor 1022 interfaces with the communication bus 1004 and the display 1020 and receives display data from the processor 1002 and converts the display data into display commands for the display 1020.

Certain embodiments may be performed as a computer program. The computer program may exist in a variety of forms both active and inactive. For example, the computer program can exist as software program(s) comprised of program instructions in source code, object code, executable code or other formats; firmware program(s); or hardware description language (HDL) files. Any of the above can be embodied on a computer readable medium, which include storage devices and signals, in compressed or uncompressed form. Exemplary computer readable storage devices include conventional computer system RAM (random access memory), ROM (read-only memory), EPROM (erasable, programmable ROM), EPROM (electrically erasable, programmable ROM), and magnetic or optical disks or tapes. Exemplary computer readable signals, whether modulated using a carrier or not, are signals that a computer system hosting or running the present invention can be configured to access, including signals downloaded through the Internet or other networks. Concrete examples of the foregoing include distribution of executable software program(s) of the computer program on a CD-ROM or via Internet download. In a sense, the Internet itself, as an abstract entity, may be a computer readable medium. The same may be true of computer networks in general.

While the invention has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method may be performed in a different order than illustrated or simultaneously. Those skilled in the art will recognize that these and other variations are possible within the spirit and scope as defined in the following claims and their equivalents.

FIG. 10 illustrates a more detailed flow diagram 900 for reuse draft component 430 in accordance with another embodiment. It should be readily apparent to those of ordinary skill in the art that this flow diagram 800 represents a generalized illustration and that other steps may be added or existing steps may be removed or modified.

As shown in FIGS. 8A-B, the reuse client module 340 may be configured to receive indication that the user chooses to add material to a current document in the reuse draft component 430 by hovering over a selected section, in step 805. Subsequently, the reuse client module 340 may highlight the selected section, in step 810.

In step 815, the reuse client module 340 may receive indication that the user has expanded the associated selected section in the section viewer component 420. In step 820, the reuse client module 340 may receive a selection of individual paragraph(s) or entire selection for reuse by the user selecting the appropriate check box, as discussed above.

In step 820, the reuse client module 340 may append the selected material from step 820 to the current document in the reuse draft component 430. Subsequently, the reuse client module 340 enters an idle state waiting for user input.

For the convenience of the reader, the above description has focused on a representative sample of all possible embodiments, a sample that teaches the principles of the invention and conveys the best mode contemplated for carrying it out. The description has not attempted to exhaustively enumerate all possible variations. Further undescribed alternative embodiments are possible. It will be appreciated that many of those undescribed embodiments are within the literal scope of the following claims, and others are equivalent.

What is claimed is:

1. A method for a using at least one processor to provide a graphical user interface that enables the creation of a new electronic document using at least a portion of one or more existing electronic medical documents, the new electronic medical document including material describing an encounter between a patient and a medical service provider, the method comprising:

adding to the new electronic medical document text resulting from performing speech-to-text processing on input speech of the medical service provider describing the encounter between the patient and the medical service provider;

receiving a query identifying one or more search parameters via the graphical user interface;

retrieving the one or more existing electronic medical documents in response to determining that the one or more existing electronic medical documents satisfy the one or more search parameters identified in the query;

displaying on a computer display, a list of medical document sections and, associated with each one section of the medical document sections of the list, a title of the one section and one or more excerpts each comprising text that was included in the one section in at least one of the one or more existing electronic medical documents, wherein the medical document sections included in the list include a first section, wherein the one or more excerpts included in the first section include a first excerpt and a second excerpt that were included in the first section in a first existing electronic medical document of the one or more existing electronic medical documents, and wherein the text of each of the first ant second excerpts is less than all text included in the first section in the first existing electronic medical document;

for each of the displayed excerpts, displaying at least one corresponding indicator on the computer display, each displayed indicator including information indicating whether the indicator is in a selected state or an unselected state;

enabling a user to operate the graphical user interface so as to selectively alter the states of the displayed indicators; and for each one section of the list of medical document sections and for each one of at least one displayed excerpt, of the one section, for which the user has put a corresponding indicator in the selected state, copying text of the one displayed excerpt into a medical document section of the new electronic medical document corresponding to the one section.

2. The method of claim 1, further comprising:
in response to receiving the input from the user indicating that the user has finished altering the states of the displayed indicators, for each displayed excerpt for which a corresponding indicator is in the unselected state, refraining from copying into the new electronic medical document a portion of one or more of the existing electronic medical documents corresponding to that displayed excerpt.

3. The method of claim 1, further comprising:
displaying on the computer display at least one indicator corresponding to at least one section of the medical document section of the list; and
in response to receiving user input causing the at least one indicator corresponding to a medical document section to be put in the selected state, causing respective indicators for one or more displayed excerpts associated with the medical document section to be put in the selected state.

4. The method of claim 1, further comprising:
automatically segmenting the one or more existing electronic medical documents into portions corresponding to the displayed excerpts.

5. A system for providing a graphical user interface that enables the creation of a new electronic medical document using at least a portion of one or more existing electronic medical documents, the new electronic medical document including material describing an encounter between a patient and a medical service provider, the system comprising:

at least one processor configured to perform acts of:
adding to the new electronic medical document text resulting from performing speech-to-text processing on input speech of the medical service provider describing the encounter between the patient and the medical service provider;

receiving a query identifying one or more search parameters via the graphical user interface;

retrieving the one or more existing electronic medical documents in response to determining that the one or more existing electronic medical documents satisfy the one or more search parameters identified in the query;

displaying, on a computer display, of a list of medical document sections and, associated with each one section of the medical document sections of the list, a title of the one section and one or more excerpts each comprising text that was included in the one section in at least one of the one or more existing electronic medical documents, wherein the medical document sections included in the list include a first section, wherein the one or more excerpts included in the first section include a first excerpt and a second excerpt that were included in the first section in a first existing electronic medical document of the one or more existing electronic medical documents, and wherein the text of each of the first and second excerpts is less than all text included in the first section in the first existing electronic medical document;

for each of the displayed excerpts, displaying at least one corresponding indicator to be displayed on the computed display, each displayed indicator including information indicating whether the indicator is in a selected state or an unselected state, enabling a user to operate the graphical user interface so as to selectively alter the states of the displayed indicators; and for each one section of the list of medical document sections and for each one of at least one displayed excerpt, of the one section, for which the user has put a corresponding indicator in the selected state, copying text of the one displayed excerpt into a medical document section of the new electronic medical document corresponding to the one section.

6. The system of claim 5, wherein the at least one processor is further configured to perform an act of, in response to receiving an input from the user indicating that the user has finished altering the states of the displayed indicators, for each displayed excerpt for which a corresponding indicator is in the unselected state, refraining from copying into the new electronic medical document a portion of one or more of the existing electronic medical documents corresponding to that displayed excerpt.

7. The system of claim 5, wherein the at least one processor is further configured to carry out an act of automatically segmenting the one or more existing electronic medical document into the portions corresponding to the displayed excerpts.

8. A non-transitory, computer-readable medium encoded with instructions that, when executed by at least one processor, cause the at least one processor to perform a method for providing a graphical user interface that enables the creation of a new electronic medical document using at least a portion of one or more existing electronic documents, the new electronic medical document including material describing an encounter between a patient and a medical service provider, the method comprising:
  adding to the new electronic medical document text resulting from performing speech-to-text processing on input speech of the medical service provider describing the encounter between the patient and the medical service provider;
  receiving a query identifying one or more search parameters via the graphical user interface; and
  retrieving the one or more existing electronic medical documents in response to determining that the one or more existing electronic medical documents satisfy the one or more search parameters identified in the query;
  display, on a computer display, a list of medical document sections and, associated with each one section of the medical document sections of the list, a title of the one section and one or mor excerpts comprising text that was included in the one section in at least one of the one or more existing electronic medical documents, wherein the medical document sections included in the list include a first section, wherein the one or more excerpt included in the first section include a first excerpt and a second excerpt that were included in the first section in a first existing electronic medical document of the one or more existing electronic medical documents, and wherein the text of each of the first and second excerpts is less than all text included in the first section in the first existing electronic medical document;
  for each of the displayed excerpts, displaying at least one corresponding indicator on the computer display, each displayed indicator including information indicating whether the indicator is in a selected state or an unselected state;
  enabling a user to operate the graphical user interface so as to selectively alter the states of the displayed indicators; and
  for each one section of the list of medical document sections and for each one of at least one displayed excerpt, of the one section, for which the user has put a corresponding indicator in the selected state, copying text of the one displayed excerpt into a medical document section of the new electronic medical document corresponding to the one section.

9. The computer-readable medium of claim 8, wherein the method further comprises:
  in response to receiving the input from the user indicating that the user has finished altering the states of the displayed indicators, for each displayed excerpt for which a corresponding indicator is in the unselected state, refraining from copying into the new electronic medical document a portion of one or more of the existing electronic medical document corresponding to that displayed excerpt.

10. The computer-readable medium of claim 8, wherein the method further comprises:
  displaying on the computer display at least one indicator corresponding to at least one section of the medical document sections of the list; and
  in response to receiving user input causing the at least one indicator corresponding to a medical document section to be put in the selected state, causing respective indicators for on or more displayed excerpts associated with the medical document section to be put in the selected state.

11. The computer-readable medium of claim 8, wherein the method further comprises:
  automatically segmenting the one or more existing electronic medical documents into portions corresponding to the displayed excerpts.

12. The method of claim 1, wherein:
receiving the query identifying the one or more search parameters comprises receiving a query identifying a dictation source; and
determining that the one or more existing electronic medical documents satisfy the one or more search parameters comprises determining that the one or more existing electronic medical documents were dictated by the dictation source.

13. The method of claim 12, wherein:
receiving a query identifying a dictation source comprises receiving input identifying a medical department; and
determining that the one or more existing electronic medical documents were dictated by the dictation source comprises determining that the one or more existing electronic medical documents were dictated by an individual associated with the medical department.

14. The method of claim 12, wherein:
receiving a query identifying a dictation source comprises receiving input identifying an individual; and
determining that the one or more existing electronic medical documents were dictated by the dictation source comprises determining that the one or more existing electronic medical documents were dictated by the individual.

15. The method of claim 1, wherein the first excerpt and the second excerpt are paragraphs that were included in the first section in the first existing electronic medical document.

16. The method of claim 4, wherein automatically segmenting the one or more existing electronic medical documents into portions corresponding to the displayed excerpts comprises, for the first section of the first existing electronic medical document, segmenting text included in the first section in the first existing electronic medical document into the first excerpt and the second excerpt, the first excerpt comprising one paragraph and the second excerpt comprising another paragraph.

17. The method of claim 1, wherein copying text of the one displayed excerpt into medical document section of the new electronic medical document corresponding to the one section comprises appending text of the one displayed excerpt to the text of the medical document section corresponding to the one section.

* * * * *